(12) United States Patent
Yasueda et al.

(10) Patent No.: US 6,333,045 B1
(45) Date of Patent: Dec. 25, 2001

(54) AQUEOUS LIQUID PHARMACEUTICAL COMPOSITION COMPRISED OF GATIFLOXACIN

(75) Inventors: Shinichi Yasueda; Katsuhiro Inada, both of Kobe (JP)

(73) Assignees: Senju Pharmaceutical Co., Ltd., Osaka; Kyorin Pharmaceutical Co., Ltd., Tokyo, both of (JP)

( * ) Notice: Subject to any disclaimer, the term of this patent is extended or adjusted under 35 U.S.C. 154(b) by 0 days.

(21) Appl. No.: 09/529,882

(22) PCT Filed: Aug. 20, 1999

(86) PCT No.: PCT/JP99/04483
  § 371 Date: Apr. 21, 2000
  § 102(e) Date: Apr. 21, 2000

(87) PCT Pub. No.: WO00/10570
  PCT Pub. Date: Mar. 2, 2000

(30) Foreign Application Priority Data

Aug. 21, 1998 (JP) .................................................. 10/235432

(51) Int. Cl.$^7$ .......................... A61F 13/00; A61K 31/495
(52) U.S. Cl. .......................... 424/434; 424/400; 424/422; 424/427; 424/437; 424/78.04; 514/254
(58) Field of Search ................................. 424/400, 78.04, 424/422, 427, 434, 437

(56) References Cited

U.S. PATENT DOCUMENTS

| | | | |
|---|---|---|---|
| 4,528,287 | * 7/1985 | Itoh et al. | 514/254 |
| 4,780,465 | 10/1988 | Ogata et al. | 514/254 |
| 4,980,470 | 12/1990 | Masuzawa et al. | 544/363 |
| 5,043,450 | 8/1991 | Masuzawa et al. | 546/156 |

OTHER PUBLICATIONS

Tanaka, Masatoshi et al., "Emergence of In Vitro Resistance to Fluoroquinolones in *Neisseria gonorrhoeae* Isolated in Japan", Antimicrobial Agents and Chemotherapy, 1995, vol. 39, No. 10, pp. 2367–2370.

Kubo Shuta et al., "Enhanced Chemiluminescence Response of Polymorphonuclear Leukocytes by New Quinolone Antimicrobials", Chemotherapy, 1994, vol. 40, No. 5, pp. 333–336.

Sasaki, Hitoshi et al., "Different Effects of Absorption Promoters on Corneal and Conjunctival Penetration of Ophthalmic Beta–Blockers", Pharmaceutical Research, 1995, vol. 12, No. 8, pp. 1146–1150.

Grass George M., et al., "Mechanisms of Corneal Drug Penetration 1: In Vivo and In Vitro Kinetics", Journal of Pharmaceutical Sciences, Jan. 1988, vol. 77, No. 1, pp. 3–14.

Grass George M., et al., "Effects of Calcium Chelating Agents on Corneal Permeability", Investigative Ophthalmology & Visual Science/Jan. 1985, vol. 26, pp. 110–113.

Podder, Samir K., et al. "Improving the Safety of Topically Applied Timolol in the Pigmented Rabbit Through Manipulation of Formulation Composition", Exp. Eye Res. (1992), 54, pp. 747–757.

* cited by examiner

Primary Examiner—Thurman K. Page
Assistant Examiner—Charesse L. Evans
(74) Attorney, Agent, or Firm—Wenderoth, Lind & Ponack, L.L.P.

(57) ABSTRACT

There is provided an aqueous liquid pharmaceutical composition which comprises Gatifloxacin (chemical nomenclature: (±)-1-cyclopropyl-6-fluoro-1,4-dihydro-8-methoxy-7-(3-methyl-1-piperazinyl)-4-oxo-3-quinoline carboxylic acid) or its salt and disodium edetate. Further, there are provided a method for raising corneal permeability of Gatifloxacin, a method for preventing precipitation of Gatifloxacin crystals, and a method for preventing coloration of Gatifloxacin by incorporating disodium edetate into an aqueous liquid preparation containing Gatifloxacin or its salt.

11 Claims, No Drawings

AQUEOUS LIQUID PHARMACEUTICAL COMPOSITION COMPRISED OF GATIFLOXACIN

FIELD OF THE INVENTION

The present invention relates to an aqueous liquid pharmaceutical composition comprising as a main component a quinolone carboxylic acid derivative, Gatifloxacin (chemical nomenclature: (±)-1-cyclopropyl-6-fluoro-1,4-dihydro-8-methoxy-7-(3-methyl-1-piperazinyl)-4-oxo-3-quinoline carboxylic acid). Further, the present invention relates to a method for raising corneal permeability of Gatifloxacin, a method for preventing precipitation of Gatifloxacin crystals, and a method for preventing coloration of Gatifloxacin.

BACKGROUND OF THE INVENTION

Gatifloxacin is a new quinolone antimicrobial agent which is recognized to exhibit a strong antimicrobial activity against not only Gram-negative bacteria but also Gram-positive bacteria, anaerobes and mycoplasmas. Then, it has been proposed to apply it to ophthalmological infectious diseases such as conjunctivitis, dacryocystitis, hordeolum etc. and otorhinological infectious diseases such as otitis externa, otitis media, sinusitis etc (see JP-B 8-9597).

For designing a pharmaceutical preparation in the form of eye drops containing an antimicrobial agent, an index is to raise corneal permeability of the agent to increase the amount of the agent to transfer to aqueous humor. However, in general, the agent applied to eyes can scarcely pass into inside of the eyes because of dilution with tears and the barrier function of corneas. Then, as a method of improving corneal permeability of the agent, a method using an absorption enhancer has been proposed. In addition, a method using a viscous base material has been proposed to increase the agent-retentivity at the anterior ocular segment.

OBJECTS OF THE INVENTION

With regard to Gatifloxacin, although its application. to ophthalmological or otorhinological infectious diseases has been proposed, there is no report about a study of an aqueous liquid pharmaceutical composition thereof for topical administration, which can be actually applied to eyes, for example, its passing into inside of eyes, stability, etc.

In view of these circumstances, an object of the present invention is to permit actual application of Gatifloxacin in ophthalmological or otorhinological field, in particular, to provide an aqueous liquid pharmaceutical composition comprising as an effective component Gatifloxacin.

SUMMARY OF THE INVENTION

The present inventors have intensively studied to apply Gatifloxacin in ophthalmological field and, consequently, have found that this objective can be achieved by coexistence of Gatifloxacin with disodium edetate.

Disodium edetate is considered to lower the calcium concentration in corneal epithelium cells and expanding intercellular spaces, thereby accelerating passing of a water-soluble medicament into inside of eyes. However, a rise in corneal permeability of a medicament depends on a concentration of disodium edetate (Journal of Pharmaceutical Science, 77: 3–14, 1988) and, normally, at present, disodium edetate should be used at a high concentration as much as 0.5% (Investigative Ophthalmology & Visual Science, 66: 110–113, 1985; Experimental Eye Research, 54: 747–757, 1992; Pharmaceutical Research, 12: 1146–1150). Nevertheless, the present inventors have found that corneal permeability of Gatifloxacin can be improved at a lower concentration of disodium edetate.

Further, it has been known that the solubility of Gatifloxacin depends on pH and its solubility at about physiological pH is very low. Then, in order to dissolve a sufficient amount of Gatifloxacin in an aqueous liquid pharmaceutical composition, pH of the composition should be adjusted to an acidic or alkaline range, which causes a problem such as irritation upon topical administration. However, the present inventors also have found that the solubility of Gatifloxacin at about physiological pH is improved by coexistence thereof with disodium edetate.

The present invention has been completed based on these present inventors' novel findings and, according to the present invention, there is provided an aqueous liquid pharmaceutical composition which comprises Gatifloxacin or its salt and disodium edetate. In particular, the aqueous liquid pharmaceutical composition of the present invention is an aqueous solution containing Gatifloxacin or its salt and disodium edetate.

Further, the present invention provides a method for raising corneal permeability of Gatifloxacin which comprises incorporating disodium edetate into eye drops containing Gatifloxacin or its salt; a method for preventing precipitation of Gatifloxacin crystals which comprises incorporating disodium edetate into an aqueous liquid preparation containing Gatifloxacin or its salt; and a method for preventing coloration of Gatifloxacin which comprises incorporating disodium edetate into an aqueous liquid preparation containing Gatifloxacin or its salt.

This object as well as other objects and advantages of the present invention will become apparent to those skilled in the art from the following description.

DETAILED DESCRIPTION OF THE INVENTION

In the present invention, Gatifloxacin or its salt is used as the effective component. Examples of the salt of Gatifloxacin used in the present invention include those with inorganic acids such as hydrochloric acid, sulfuric acid, phosphoric acid, etc.; those with organic acids such as methanesulfonic acid, lactic acid, oxalic acid, acetic acid, etc.; or those with sodium, potassium, magnesium, calcium, aluminum, cerium, chromium, cobalt, copper, iron, zinc, platinum, silver, etc.

Normally, the amount of Gatifloxacin or its salt (hereinafter sometimes simply referred to as "Gatifloxacin") to be formulated in the aqueous liquid pharmaceutical composition of the present invention is varied according to the degree of infection of a particular subject, but normally, Gatifloxacin is formulated within the range of 0.1 to 1.0 w/v %, preferably 0.1 to 0.8 w/v %, more preferably 0.3 to 0.5 w/v %.

Normally, disodium edetate is formulated in an amount of 0.001 to 0.2 w/v %, preferably 0.005 to 0.1 w/v %, more preferably 0.01 to 0.1 w/v %.

Normally, the aqueous liquid pharmaceutical composition of the present invention is adjusted to pH 5 to 8, preferably pH 5.5 to 7.5, more preferably pH 6 to 7.

If necessary, the aqueous liquid pharmaceutical composition of the present invention may further contain appropriate additives, for example, an isotonic agent. (e.g., sodium chloride, potassium chloride, boric acid, glycerin, propylene glycol, mannitol, sorbitol, glucose etc.); a buffer solution (e.g., phosphate buffer solution, acetate butter solution, borate buffer solution, citrate buffer solution, glutamic acid, ε-aminocapronic acid, etc.); a preservative (e.g., benzalkonium chloride, benzethonium chloride, chlorhexidine gluconate, chlorobutanol, benzyl alcohol, sodium dehydroacetate, p-hydroxybenzoate, etc.), a thickening agent (e.g., methylcellulose, hydroxyethyl cellulose, hydroxypropyl methylcellulose, carboxymethylcellulose, sodium hyaluronate, carboxyvinyl polymer, polyvinyl alcohol, polyvinyl pyrrolidone, Macrogol (polyethylene glycol), etc.), a pH adjusting agent (e.g., hydrochloric acid, sodium hydroxide, acetic acid, phosphoric acid, etc.), and the like.

The aqueous liquid pharmaceutical composition of the present invention can be produced by a per se known method. For example, it can be produced by the process described in the section of "Ophthalmic Solutions" or "Liquids and Solutions", General Rules for Preparations, The Japanese Pharmacopoeia Thirteenth Edition.

The aqueous liquid pharmaceutical composition of the present invention has antimicrobial activity and can be used for prophylaxis and therapy of blepharitis, hordeolum, dacryocystitis, conjunctivitis, tarsitis, keratitis, corneal ulcer, postoperative infection, and the like. For this purpose, the composition can be instilled in the eye about three times a day at a dosage of one drop per once. For otitis externa or otitis media, normally, the composition can be instilled in the ear twice a day at a dosage of 6 to 10 drops per once. Further, for sinusitis, normally, the composition can be sprayed and inhaled three times every other day in a week at a dosage of 2 to 4 ml per once, or can be administered in the maxillary sinus once a week at a dosage of 1 ml per once. The dosage can be increased or decreased according to the degree of a particular disease condition.

The present invention will be further illustrated by the following experiments and examples, but the present invention is not limited thereto.

Experiment 1

Effect of disodium edetate on transfer of Gatifloxacin to aqueous humor

Method

According to the formulations of Table 1, eye drops of Gatifloxacin were prepared (formulations A–C). Each of the eye drops (50 μl/eye) was instilled once in the eyes of male Japanese albino rabbits (body weight: about 2 kg). At one hour after the instillation, the aqueous humor was collected and the Gatifloxacin concentration was determined by HPLC.

TABLE 1

| Formulations | A | B | C |
| --- | --- | --- | --- |
| Gatifloxacin | 0.5 g | 0.5 g | 0.5 g |
| Disodium edetate | — | — | 0.05 g |
| Sodium chloride | 0.9 g | 0.9 g | 0.9 g |
| Hydrochloric acid | q.s. | q.s. | q.s. |
| Sodium hydroxide | q.s. | q.s. | q.s. |
| Sterilized purified water | to total 100 ml | to total 100 ml | to total 100 ml |
| pH | 7.0 | 6.0 | 6.0 |

Results

The concentration of Gatifloxacin in the aqueous humor at one hour after the instillation is shown in Table 2.

When pH dropped, the amount of Gatifloxacin transferred to the aqueous humor decreased. For the formulation adjusted to pH 6.0 (formulation C), the amount of Gatifloxacin transferred to the aqueous humor increased by about 1.2 times and 1.5 times as much as those of the formulations A (pH 7.0) and B (pH 6.0) which were used as controls, respectively.

Since the concentration of disodium edetate normally used for raising corneal permeability is 0.5 w/v %, these results show that corneal permeability of Gatifloxacin has been improved even by using disodium edetate in 1/10 amount as much as that normally used.

TABLE 2

| Formulations | Gatifloxacin concentration in aqueous humor (μg/ml) |
| --- | --- |
| A | 1.61 ± 0.43 |
| B | 1.30 ± 0.42 |
| C | 1.93 ± 0.95 |

Experiment 2

Effect of disodium edetate on precipitation of Gatifloxacin crystals

Method

According to the formulations of Table 3, aqueous liquid preparations of Gatifloxacin were prepared (formulations B–D). Each solution was filled in 5 ml glass ampoules. The ampoules were subjected to freezing at −30° C. (overnight) and then thawing at room temperature repeatedly to observe precipitation of Gatifloxacin crystals.

TABLE 3

| Formulations | B | C | D |
| --- | --- | --- | --- |
| Gatifloxacin | 0.5 g | 0.5 g | 0.5 g |
| Disodium edetate | — | 0.05 g | 0.1 g |
| Sodium chloride | 0.9 g | 0.9 g | 0.9 g |
| Hydrochloric acid | q.s. | q.s. | q.s. |
| Sodium hydroxide | q.s. | q.s. | q.s. |
| Sterilized purified water | to total 100 ml | to total 100 ml | to total 100 ml |
| pH | 6.0 | 6.0 | 6.0 |

Results

In the formulation in which disodium edetate was not formulated (formulation B), crystals were precipitated when freezing and thawing were repeated twice to three times. On the other hand, when disodium edetate was formulated (formulations C and D), no precipitation of crystals was recognized even when freezing and thawing were repeated ten times.

These results show that precipitation of Gatifloxacin crystals under storage conditions at a low temperature is prevented by formulating disodium edetate in an aqueous liquid preparation of Gatifloxacin.

Experiment 3

Effect of disodium edetate on preventing coloration of Gatifloxacin

Method

Sodium chloride (0.86 g) and 0.1 mol/liter hydrochloric acid (5.2 ml) were added to sterilized purified water (80 ml) in a stainless steel (SUS316) beaker of 8 cm diameter and the mixture was stirred. Then, Gatifloxacin (0.32 g) and disodium edetate (at a final concentration of 0%, 0.001%, 0.005%, 0.01% or 0.05%) were added thereto and dissolved therein. The solution was adjusted to pH 6.5 with 0.1 mol/liter sodium hydroxide and the total volume was made up to 100 ml to obtain an aqueous liquid preparation of Gatifloxacin. A color difference between the aqueous liquid preparation and sterilized purified water was determined with a differential calorimeter (Chroma meter CT-210C manufactured by Minolta, light source Lab table system). As a control, an aqueous liquid preparation of Gatifloxacin prepared in a glass beaker was used.

Results

The color difference determined is shown in Table 4.

The aqueous liquid preparation prepared in the glass beaker and used as the control had the color difference of 1.9 to 2.0 and a pale yellow color. On the other hand, the aqueous liquid preparation prepared in the stainless steel beaker had the color difference of 3.17 in case that disodium edetate was not added and 2.42 in case that 0.01% of disodium edetate was added. They had a light yellow color and a pale yellow color, respectively. Thus, they were discolored by formulating disodium edetate.

In view of these results, it is considered that Gatifloxacin is colored by the metal ion dissolved in the preparation from the stainless steel beaker. Further, these results show that addition of disodium edetate can prevent coloration of Gatifloxacin.

TABLE 4

| Concentration of | Color Difference | |
|---|---|---|
| disodium edetate (%) | Stainless Steel Beaker | Glass Beaker |
| 0 | 3.17 | 1.90 |
| 0.001 | 3.08 | 1.93 |
| 0.005 | 3.05 | 2.02 |
| 0.01 | 2.42 | 1.94 |
| 0.05 | 2.19 | 1.93 |

EXAMPLE 1

According to a conventional method, an aqueous solution for eye drops, ear drops and nasal drops having the following formulation was prepared.

| Ingredients | Amount |
|---|---|
| Gatifloxacin | 0.5 g |
| Disodium edetate | 0.1 g |
| Sodium chloride | 0.9 g |
| Hydrochloric acid | q.s. |
| Sodium hydroxide | q.s. |
| Sterilized purified water | up to 100 ml |
| pH | 7.0 |

EXAMPLE 2

According to a conventional method, an aqueous solution for eye drops, ear drops and nasal drops having the following formulation was prepared.

| Ingredients | Amount |
|---|---|
| Gatifloxacin | 0.5 g |
| Disodium edetate | 0.05 g |
| Sodium chloride | 0.9 g |
| Hydrochloric acid | q.s. |
| Sodium hydroxide | q.s. |
| sterilized purified water | up to 100 ml |
| pH | 7.0 |

EXAMPLE 3

According to a conventional method, an aqueous solution for eye drops, ear drops and nasal drops having the following formulation was prepared.

| Ingredients | Amount |
|---|---|
| Gatifloxacin | 0.5 g |
| Disodium edetate | 0.1 g |
| Sodium dihydrogen phosphate | 0.1 g |
| Sodium chloride | 0.9 g |
| Hydrochloric acid | q.s. |
| Sodium hydroxide | q.s. |
| Sterilized purified water | up to 100 ml |
| pH | 7.0 |

EXAMPLE 4

According to a conventional method, an aqueous solution for eye drops, ear drops and nasal drops having the following formulation was prepared.

| Ingredients | Amount |
|---|---|
| Gatifloxacin | 0.3 g |
| Disodium edetate | 0.05 g |
| Sodium chloride | 0.9 g |
| Hydrochloric acid | q.s. |
| Sodium hydroxide | q.s. |
| Sterilized purified water | up to 100 ml |
| pH | 6.0 |

EXAMPLE 5

According to a conventional method, an aqueous solution for eye drops, ear drops and nasal drops having the following formulation was prepared.

| Ingredients | Amount |
|---|---|
| Gatifloxacin | 0.5 g |
| Sodium edetate | 0.01 g |
| Glycerin | 2.6 g |
| Benzalkonium chloride | 0.005 g |
| Hydrochloric acid | q.s. |
| Sodium hydroxide | q.s. |
| Sterilized purified water | up to 100 ml |
| pH | 7.5 |

EXAMPLE 6

According to a conventional method, an aqueous solution for eye drops, ear drops and nasal drops having the following formulation was prepared.

| Ingredients | Amount |
| --- | --- |
| Gatifloxacin | 0.5 g |
| Sodium edetate | 0.05 g |
| Sodium chloride | 0.9 g |
| Hydrochloric acid | q.s. |
| Sodium hydroxide | q.s. |
| Sterilized purified water | up to 100 ml |
| pH | 5.5 |

EXAMPLE 7

According to a conventional method, an aqueous solution for eye drops, ear drops and nasal drops having the following formulation was prepared.

| Ingredients | Amount |
| --- | --- |
| Gatifloxacin | 0.3 g |
| Disodium edetate | 0.05 g |
| Sodium chloride | 0.9 g |
| Hydroxypropylmethyl cellulose | 0.1 g |
| Methyl p-hydroxybenzoate | 0.026 g |
| Propyl p-hydroxybenzoate | 0.014 g |
| Hydrochloric acid | q.s. |
| Sodium hydroxide | q.s. |
| Sterilized purified water | up to 100 ml |
| pH | 6.0 |

EXAMPLE 8

According to a conventional method, an aqueous solution for eye drops, ear drops and nasal drops having the following formulation was prepared.

| Ingredients | Amount |
| --- | --- |
| Gatifloxacin | 0.5 g |
| Disodium edetate | 0.01 g |
| Sodium chloride | 0.83 g |
| Benzalkonium chloride | 0.005 g |
| Hydrochloric acid | q.s. |
| Sodium hydroxide | q.s. |
| Sterilized purified water | up to 100 ml |
| pH | 5.5 |

EXAMPLE 9

According to a conventional method, an aqueous solution for eye drops, ear drops and nasal drops having the following formulation was prepared.

| Ingredients | Amount |
| --- | --- |
| Gatifloxacin | 0.3 g |
| Disodium edetate | 0.01 g |
| Sodium chloride | 0.86 g |
| Benzalkonium chloride | 0.005 g |
| Hydrochloric acid | q.s. |
| Sodium hydroxide | q.s. |
| Sterilized purified water | up to 100 ml |
| pH | 6.0 |

As shown in Experiment 1, according to the eye drops of the present invention, corneal permeability of the effective component, Gatifloxacin, can be improved even by using disodium edetate in 1/10 amount as much as that normally used. Further, as shown in Experiment 2, the aqueous liquid preparation of the present invention can. prevent precipitation of Gatifloxacin crystals under storage conditions as a low temperature. Furthermore, as shown in Experiment 3, coloration of Gatifloxacin by a metal ion can be prevented. Thus, the aqueous liquid preparation of the present invention is very useful.

What is claimed is:

1. An aqueous liquid pharmaceutical composition which comprises Gatifloxacin or its salt and disodium edetate.

2. The aqueous liquid pharmaceutical composition according to claim 1, wherein pH of the composition is within the range of 5 to 8.

3. The aqueous liquid pharmaceutical composition according to claim 1, where the composition is in the form of eye drops.

4. The aqueous liquid pharmaceutical composition according to claim 1, where the composition is in the form of ear drops.

5. The aqueous liquid pharmaceutical composition according to claim 1, where the composition is in the form of nasal drops.

6. A method for raising corneal permeability of Gatifloxacin which comprises incorporating disodium edetate into eye drops containing Gatifloxacin or its salt.

7. A method for preventing precipitation of Gatifloxacin crystals which comprises incorporating disodium edetate into an aqueous liquid preparation containing Gatifloxacin or its salt.

8. A method for preventing coloration of Gatifloxacin which comprises incorporating disodium edetate into an aqueous liquid preparation containing Gatifloxacin or its salt.

9. The aqueous liquid pharmaceutical composition according to claim 2, where the composition is in the form of eye drops.

10. The aqueous liquid pharmaceutical composition according to claim 2, where the composition is in the form of ear drops.

11. The aqueous liquid pharmaceutical composition according to claim 2, where the composition is in the form of nasal drops.

* * * * *

UNITED STATES PATENT AND TRADEMARK OFFICE
CERTIFICATE OF CORRECTION

PATENT NO. : 6,333,045 C1
APPLICATION NO. : 90/011509
DATED : October 25, 2011
INVENTOR(S) : Shinichi Yasueda et al.

Page 1 of 1

It is certified that error appears in the above-identified patent and that said Letters Patent is hereby corrected as shown below:

Column 2, line 1, "above" should be changed to --about--.

Signed and Sealed this
Tenth Day of January, 2012

David J. Kappos
*Director of the United States Patent and Trademark Office*

UNITED STATES PATENT AND TRADEMARK OFFICE
CERTIFICATE OF CORRECTION

PATENT NO.        : 6,333,045 C1
APPLICATION NO.   : 90/011509
DATED             : October 25, 2011
INVENTOR(S)       : Shinichi Yasueda et al.

Page 1 of 1

It is certified that error appears in the above-identified patent and that said Letters Patent is hereby corrected as shown below:

Column 2, line 22, "14" should read --15--.

Signed and Sealed this
Fifteenth Day of May, 2012

David J. Kappos
*Director of the United States Patent and Trademark Office*

(12) EX PARTE REEXAMINATION CERTIFICATE (8636th)
United States Patent
Yasueda et al.

(10) Number: US 6,333,045 C1
(45) Certificate Issued: Oct. 25, 2011

(54) AQUEOUS LIQUID PHARMACEUTICAL COMPOSITION COMPRISED OF GATIFLOXACIN

(75) Inventors: Shinichi Yasueda, Kobe (JP); Katsuhiro Inada, Kobe (JP)

(73) Assignees: Senju Pharmaceutical Co., Ltd.; part interest; Kyorin Pharmaceutical Co., Ltd.; part interest

Reexamination Request:
No. 90/011,509, Feb. 25, 2011

Reexamination Certificate for:
Patent No.: 6,333,045
Issued: Dec. 25, 2001
Appl. No.: 09/529,882
Filed: Apr. 21, 2000

(22) PCT Filed: Aug. 20, 1999

(86) PCT No.: PCT/JP99/04483
§ 371 (c)(1),
(2), (4) Date: Apr. 21, 2000

(87) PCT Pub. No.: WO00/10570
PCT Pub. Date: Mar. 2, 2000

(51) Int. Cl.
*A61K 47/16* (2006.01)
*A61K 9/00* (2006.01)
*A61K 31/496* (2006.01)
*A61K 47/18* (2006.01)
*C07D 215/00* (2006.01)
*C07D 215/56* (2006.01)

(52) U.S. Cl. .......... 424/434; 424/400; 424/422; 424/427; 424/437; 424/78.04

(58) Field of Classification Search .......... 424/434
See application file for complete search history.

(56) References Cited

U.S. PATENT DOCUMENTS

| | | | |
|---|---|---|---|
| 4,551,456 A | 11/1985 | Katz | |
| 4,780,465 A | 10/1988 | Ogata et al. | |
| 4,980,470 A | 12/1990 | Masuzawa et al. | |
| 6,057,290 A | 5/2000 | Fukiage et al. | |
| 6,214,800 B1 | 4/2001 | Fukiage et al. | |
| 6,551,999 B1 | 4/2003 | Fukiage et al. | |

FOREIGN PATENT DOCUMENTS

| | | |
|---|---|---|
| EP | 0 337 328 | 10/1989 |
| EP | 0 872 236 | 10/1998 |
| JP | 63-190826 | 8/1988 |
| JP | 3-34925 | 2/1991 |
| JP | 9-124484 | 5/1997 |
| JP | 10-147566 | 6/1998 |
| WO | 98/30221 | 7/1998 |

OTHER PUBLICATIONS

Yakuzaigaku I Chozai, Seizai, Japan, Asakura Shten, Apr. 15, 1995, pp. 121–123, with English language translation provided.

Iyakuhin Tenkazai Youran, Japan, Yakuzaijihosha, 1992, cover page, p. 17, with English language translation provided.

Riley et al., "The Physicochemical Properties of Quinolone Antimicrobials Variously Substituted at C–7. Implications in the Development of Liquid Dosage Forms", Quinolones. J.R. Prous Science Publishers, S.A. (1989), pp. 21–36.

G. Grass et al.,"Effects of Calcium Chelating Agents on Corneal Permeability", Investigative Ophthamology & Visual Science, vol. 26, Jan. 1985, pp. 110–113.

D. Griffith, "Improvement of the Color Stability of Parenteral Solutions of Papaverine Hydrochloride", Journal of Pharmaceutical Sciences, vol. 56, No. 9, Sep. 1967, pp. 1197–1198.

G. Grass et al., "Mechanisms of Corneal Drug Penetration I: In Vivo and In Vitro Kinetics" Journal of Pharmaceutical Sciences, vol. 77, No. 1, Jan. 1988, pp. 3–14.

*Primary Examiner* — Dwayne Jones

(57) ABSTRACT

There is provided an aqueous liquid pharmaceutical composition which comprises Gatifloxacin (chemical nomenclature: (±)-1-cyclopropyl-6-fluoro-1,4-dihydro-8-methoxy-7-(3-methyl-1-piperazinyl)-4-oxo-3-quinoline carboxylic acid) or its salt and disodium edetate. Further, there are provided a method for raising corneal permeability of Gatifloxacin, a method for preventing precipitation of Gatifloxacin crystals, and a method for preventing coloration of Gatifloxacin by incorporating disodium edetate into an aqueous liquid preparation containing Gatifloxacin or its salt.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-3 and 8-11 are cancelled.

Claim 6 is determined to be patentable as amended.

New claims 12-16 are added and determined to be patentable.

Claims 4, 5 and 7 were not reexamined.

6. A method for raising corneal permeability of an aqueous pharmaceutical Gatifloxacin eye drop solution *comprising Gatifloxacin or its salt,* having a pH of from above 5 to about 6 containing *from about 0.3 to about 0.8 w/v% Gatifloxacin or its salt,* which comprises incorporating *about 0.01 w/v%* disodium edetate into [eye drops containing Gatifloxacin or its salt] *said Gatifloxacin eye drop solution*.

12. *An aqueous liquid pharmaceutical eye drop composition which comprises from about 0.3 to about 0.8 w/v% Gatifloxacin or its salt, about 0.01 w/v% disodium edetate, and wherein the aqueous liquid pharmaceutical composition has a pH of from about 5 to about 6.*

13. *The aqueous liquid pharmaceutical eye drop composition according to claim 12, comprising about 0.3 w/v% Gatifloxacin or its salt.*

14. *The aqueous liquid pharmaceutical eye drop composition according to claim 12, comprising about 0.5 w/v% Gatifloxacin or its salt.*

15. *The aqueous liquid pharmaceutical eye drop composition according to claim 12, comprising at least one isotonic agent selected from the group consisting of sodium chloride, potassium chloride, glycerin, mannitol and glucose.*

16. *The aqueous liquid pharmaceutical eye drop composition according to claim 14, wherein the at least one isotonic agent is sodium chloride.*

* * * * *